United States Patent [19]

Burns et al.

[11] Patent Number: 5,021,325

[45] Date of Patent: Jun. 4, 1991

[54] PHOTOGRAPHIC MATERIAL AND PROCESS COMPRISING A PYRAZOLOTRIAZOLE COUPLER

[75] Inventors: Paul A. Burns; John W. Harder, both of Rochester, N.Y.

[73] Assignee: Eastman Kodak Company, Rochester, N.Y.

[21] Appl. No.: 452,997

[22] Filed: Dec. 19, 1989

[51] Int. Cl.$^5$ .................................................. G03C 7/38
[52] U.S. Cl. .................................... 430/387; 430/386; 430/558
[58] Field of Search ..................... 430/558 R, 386, 387

[56] References Cited

U.S. PATENT DOCUMENTS

| | | | |
|---|---|---|---|
| 4,443,536 | 4/1984 | Lestina | 430/552 |
| 4,777,121 | 10/1988 | Buckland et al. | 430/386 |
| 4,835,094 | 5/1989 | Wolff et al. | 430/558 |
| 4,868,100 | 9/1989 | Nishijima | 430/558 |
| 4,916,051 | 4/1990 | Tachibana et al. | 430/558 |
| 4,920,042 | 4/1990 | Waki et al. | 430/558 |

FOREIGN PATENT DOCUMENTS

| | | |
|---|---|---|
| 0119860 | 9/1984 | European Pat. Off. |
| 0284239 | 9/1988 | European Pat. Off. |
| 0285274 | 10/1988 | European Pat. Off. |
| 1247493 | 9/1971 | United Kingdom |
| 1252418 | 11/1971 | United Kingdom |
| 1398979 | 6/1975 | United Kingdom |

*Primary Examiner*—Richard L. Schilling
*Attorney, Agent, or Firm*—Richard E. Knapp

[57] ABSTRACT

A pyrazolotriazole dye-forming coupler containing on a carbon atom in a non-coupling position a ballast group derived from and bonded through a carboxylic acid portion of an unsubstituted or substituted amino acid provides useful magenta dye images in a photographic material and process and enables simplification of manufacture of the coupler. Such couplers are useful in photographic silver halide materials and processes.

7 Claims, No Drawings

PHOTOGRAPHIC MATERIAL AND PROCESS COMPRISING A PYRAZOLOTRIAZOLE COUPLER

This invention relates to new pyrazolotriazole photographic couplers that comprise a new ballast group that enables simplification of manufacture of the coupler and to photographic materials and processes comprising such couplers.

Various pyrazolotriazole photographic couplers are known in the photographic art. These couplers are known to be useful in photographic materials and processes to provide magenta dye images upon oxidative coupling with a color developing agent. Such pyrazolotriazole couplers are described in, for example, U.S. Pat. Nos. 4,777,121 and 4,443,536 and U.K. Patent Specification Nos. 1,247,493; 1,252,418 and 1,398,979 and European Patent Application No. 119,860.

Such pyrazolotriazole couplers have been expensive to manufacture due at least in part to the multiple step synthesis that is required, especially for pyrazolotriazole couplers that have required a ballast group. It has been desirable to provide a pyrazolotriazole coupler and photographic materials and processes that use such a coupler that are simpler to manufacture. It has also been desirable to provide such pyrazolotriazole couplers that provide useful coupling activity without the presence of a group that ionizes during the development process while providing useful magenta dye images having acceptable dye hue.

Although numerous pyrazolotriazole couplers are known in the photographic art, a continuing search has existed for new pyrazolotriazole couplers that improve upon existing pyrazolotriazole couplers or can be prepared by advantageous new methods.

The present invention solves these problems by means of a photographic element comprising a support bearing at least one silver halide emulsion layer having associated therewith a pyrazolotriazole dye-forming coupler wherein the coupler contains on a carbon atom in a non-coupling position a ballast group derived from and bonded through a carboxylic acid portion of an unsubstituted or substituted alpha amino acid.

The described coupler provides a pyrazolotriazole that contains a ballast that provides good coupler activity, that is it enables a desired maximum image dye density upon exposure and processing of the element, without the presence of a group that ionizes during the development process. The coupler further provides useful dye hue and enables a method of preparation that is simpler and more economical because is avoids some synthesis steps. In preparation of the couplers as described the amino acids are available as inexpensive starting materials and contain reactive groups that enable reduction of the synthesis steps that would otherwise be required to add such reactive groups in preparation of the described ballasts. For example, the amine portion of the amino acid can typically be modified with other groups without the need for adding a protective group during synthesis and without modification of the carboxylic acid portion of the amino acid. In addition, the amine portion of the resulting ballast group typically confers increased activity to the coupler to enable desired reactivity. Many of the amino acids also help provide couplers that are more easily dispersed in photographic dispersions, particularly those that have chiral portions.

In contrast to the preparation of typical ballasts for pyrazolotriazole couplers that require several synthetic steps, the described ballasts of couplers of the invention typically require merely one or two synthesis steps.

While any pyrazolotriazole coupler is useful as described, including, for example, pyrazolo [1,5-b]-1,3,5-pyrazolotriazoles and pyrazolo[3,2-c]-1,2,4-triazoles, preferred pyrazolotriazoles are pyrazolo[3,2-c]-1,2,4-triazoles.

A typical pyrazolo[3,2-c]-1,2,4-triazole is represented by the formula:

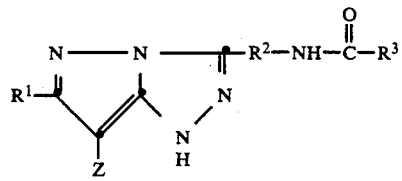

wherein
$R^1$ is an unsubstituted or substituted alkyl group, such as alkyl containing 1 to 30 carbon atoms, for example, methyl, ethyl, n-propyl, i-propyl, n-butyl, t-butyl, pentyl and eicosyl, or unsubstituted or substituted aryl group, such as an unsubstituted or substituted aryl group containing 6 to 40 carbon atoms, for example phenyl or 2,4-dimethoxyphenyl;

$R^2$ is an unsubstituted or substituted phenylene group, such as mesitylene or methoxyphenylene or substituted or unsubstituted alkylidene group such as

$R^3$ is a group derived from an unsubstituted or substituted amino acid; and,

Z is hydrogen or a coupling-off group. The acid portion of the amino acid for $R^3$ is shown as $-CO-R^3$ bonded to the NH of $-R^2-NH-$. The amine portion of the amino acid is not bonded to the pyrazolotriazole coupler moiety.

Highly preferred couplers are represented by the formula:

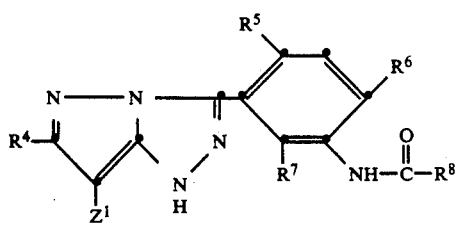

wherein
$R^4$ is methyl or t-alkyl containing 4 to 8 carbon atoms, especially t-butyl;

$R^5$, $R^6$, and $R^7$ individually are unsubstituted or substituted alkyl containing 1 to 5 carbon atoms, preferably methyl, or alkoxy containing 1 to 3 carbon atoms, such a methoxy or ethoxy;

$Z^1$ is hydrogen or a coupling-off group, especially chlorine; and, $R^8$ is a group derived from an unsubstituted or substituted amino acid.

While any amino acid is useful for formation of the described ballast group, preferred groups are HOOC—$R^3$ wherein $R^3$ is one of the following:

$$-\underset{\underset{NHCOC_9H_{19}\text{-}\underline{n}}{|}}{CH}(CH_2)_2SO_2CH_3$$

$$-\underset{\underset{NHCOC_{11}H_{23}\text{-}\underline{n}}{|}}{CH}(CH_2)_2SO_2CH_3$$

$$-\underset{\underset{NHCOC_{11}H_{23}\text{-}\underline{n}}{|}}{CH}(CH_2)_2SOCH_3$$

$$-\underset{\underset{NHCO(CH_2)_8CH=CH_2}{|}}{CH}(CH_2)_2SO_2CH_3$$

$$-\underset{\underset{NHCOCF_3}{|}}{CH}(CH_2)_2SO_2C_{10}H_{21}\text{-}\underline{n}$$

$$-CH_2NHCO(CH_2)_3SO_2C_{10}H_{21}\text{-}\underline{n}$$

$$-(CH_2)_{10}NHSO_2C_2H_5$$

$$-(CH_2)_{10}NHPO(OC_2H_5)_2$$

$$-CH(CH_3)NHCO_2(CH_2)_3NHSO_2C_8H_{17}\text{-}\underline{n}$$

or $$-\underset{\underset{O}{\underset{\|}{NHC-O-C_{10}H_{21}\text{-}\underline{n}}}}{CH}(CH_2)_2SO_2CH_3$$

Other useful $R^3$ groups are as follows:

$$-CH(CH_3)NHCO_2(CH_2)_3SO_2C_{10}H_{21}\text{-}\underline{n}$$

$$-(CH_2)_{10}NHCO(OCH_2CH_2)_3OCH_2C_6H_5$$

$$-\underset{\underset{HNSO_2C_{16}H_{33}\text{-}\underline{n}}{|}}{CH}(CH_2)_2SO_2CH_3$$

$$-\underset{\underset{NHCOCH_3}{|}}{CH}(CH_2)_2SO_2CH(CH_3)CO_2C_{12}H_{25}\text{-}\underline{n}$$

$$-\underset{\underset{NHCOCH_3}{|}}{CH}(CH_2)_2SO_2(CH_2)_3CO_2C_{12}H_{25}\text{-}\underline{n}$$

$$-\underset{\underset{NHCO(OCH_2CH_2)_3OC_8H_{17}\text{-}\underline{n}}{|}}{CH}(CH_2)_2SO_2CH_3$$

$$-\underset{\underset{NHCOCH_2SO_2CH(CO_2C_8H_{17}\text{-}\underline{n})CH_3}{|}}{CH}-C_3H_7\text{-i}$$

$$-\underset{\underset{NHSO_2C_{16}H_{33}\text{-}\underline{n}}{|}}{CH}(CH_2)_2CON(CH_3)_2$$

$$-\underset{\underset{NHSO_2C_{16}H_{33}\text{-}\underline{n}}{|}}{CH}CH_2OH$$

$$-\underset{\underset{NHCOCH(CH_3)NHCOCH_2SO_2C_{12}H_{25}\text{-}\underline{n}}{|}}{CH}(CH_2)_3SCH_3$$

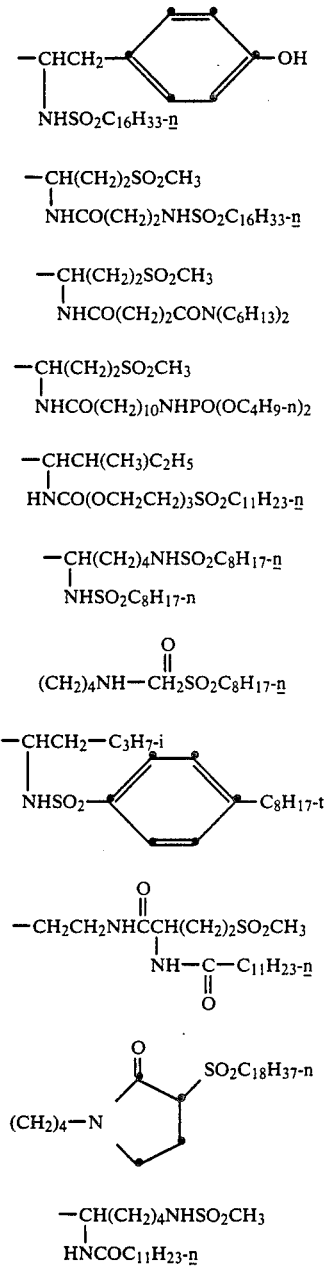

$$-\underset{\underset{NHCO(CH_2)_2NHSO_2C_{16}H_{33}\text{-}\underline{n}}{|}}{CH}(CH_2)_2SO_2CH_3$$

$$-\underset{\underset{NHCO(CH_2)_2CON(C_6H_{13})_2}{|}}{CH}(CH_2)_2SO_2CH_3$$

$$-\underset{\underset{NHCO(CH_2)_{10}NHPO(OC_4H_9\text{-n})_2}{|}}{CH}(CH_2)_2SO_2CH_3$$

$$-\underset{\underset{HNCO(OCH_2CH_2)_3SO_2C_{11}H_{23}\text{-}\underline{n}}{|}}{CH}CH(CH_3)C_2H_5$$

$$-\underset{\underset{NHSO_2C_8H_{17}\text{-n}}{|}}{CH}(CH_2)_4NHSO_2C_8H_{17}\text{-}\underline{n}$$

$$(CH_2)_4NH\underset{\underset{O}{\|}}{-}CH_2SO_2C_8H_{17}\text{-}\underline{n}$$

$$-CH_2CH_2NH\underset{\underset{O}{\|}}{C}CH(CH_2)_2SO_2CH_3$$
$$\underset{\underset{O}{\|}}{NH-C-C_{11}H_{23}\text{-}\underline{n}}$$

$$-\underset{\underset{HNCOC_{11}H_{23}\text{-}\underline{n}}{|}}{CH}(CH_2)_4NHSO_2CH_3$$

A process of forming an image in a photographic element as described containing an imagewise distribution of developable silver halide grains comprises the step of developing the element with a silver halide color developing agent.

The ballast group as described is an organic radical of such size and configuration as to confer on the coupler molecule sufficient bulk and to render the coupler substantially non-diffusible from the layer in which it is coated in a photographic element. The ballast group can be unsubstituted or substituted with groups that do not adversely affect the coupling properties of the coupler, such as alkyl, aryl, alkoxy, halogen, alkoxycarbonyl, aryloxycarbonyl, carboxy, acyl, acyloxy, aryloxycarbonyl, carbonamido, carbamoyl, alkylsulfonyl, arylsulfonyl, sulfonamido and sulfamyl groups.

The coupling position, that is the 7-position in the case of a pyrazolo[3,2-c]-1,2,4-triazole coupler, can contain hydrogen, that is the coupler can be a 4- equivalent coupler, or a coupling-off group known in the photographic art, that is the coupler can be a 2- equivalent coupler. Any coupling-off group known to be useful in the photographic art can be present in the coupling position of the coupler, such as those described in European Patent Application No. 285,274, the disclosure of which is incorporated herein by reference.

The photographic couplers of this invention can be incorporated in photographic elements and/or in photographic processing solutions, such as developer solutions, so that upon development of an exposed photographic element they will be in reactive association with oxidized color developing agent. Coupler compounds incorporated in photographic processing solutions should be of such molecular size and configuration that they will diffuse through photographic layers with the processing solution. When incorporated in a photographic element, as a general rule, the coupler compounds should be nondiffusible, that is they should be of such molecular size and configuration that they will not significantly diffuse or wander from the layer in which they are coated.

Photographic elements of this invention can be processed by conventional techniques in which color forming couplers and color developing agents are incorporated in separate processing solutions or compositions or in the element.

Photographic elements in which the compounds of this invention are incorporated can be a simple element comprising a support and a single silver halide emulsion layer or they can be multilayer, multicolor elements. The compounds of this invention can be incorporated in at least one of the silver halide emulsion layers and/or in at least one other layer, such as an adjacent layer, where they will come into reactive association with oxidized color developing agent which has developed silver halide in the emulsion layer. The silver halide emulsion layer can contain or have associated with it, other photographic coupler compounds, such as dye-forming couplers, colored masking couplers, and/or competing couplers. These other photographic couplers can form dyes of the same or different color and hue as the photographic couplers of this invention. Additionally, the silver halide emulsion layers and other layers of the photographic element can contain addenda conventionally contained in such layers.

A typical multilayer, multicolor photographic element can comprise a support having thereon a red-sensitive silver halide emulsion unit having associated therewith a cyan dye image-providing material, a green-sensitive silver halide emulsion unit having associated therewith a magenta dye image-providing material and a blue-sensitive silver halide emulsion unit having associated therewith a yellow dye image-providing material, at least one of the silver halide emulsion units having associated therewith a photographic coupler of the invention. Each silver halide emulsion unit can be composed of one or more layers and the various units and layers can be arranged in different locations with respect to one another.

The light sensitive silver halide emulsions can include coarse, regular or fine grain silver halide crystals or mixtures thereof and can be comprised of such silver halides as silver chloride, silver bromide, silver bromoiodide, silver chlorobromide, silver chloroiodide, silver chlorobromoiodide and mixtures thereof. The emulsions can be negative-working or direct-positive emulsions. They can form latent images predominantly on the surface of the silver halide grains or predominantly on the interior of the silver halide grains. They can be chemically and spectrally sensitized. The emulsions typically will be gelatin emulsions although other hydrophilic colloids are useful. Tabular grain light sensitive silver halides are particularly useful such as described in *Research Disclosure*, January 1983, Item No. 22534 and U.S. Pat. No. 4,434,226.

The support can be any support used with photographic elements. Typical supports include cellulose nitrate film, cellulose acetate film, polyvinylacetal film, polyethylene terephthalate film, polycarbonate film and related films or resinous materials as well as glass, paper, metal and the like. Typically, a flexible support is employed, such as a polymeric film or paper support. Paper supports can be acetylated or coated with baryta and/or an α-olefin containing 2 to 10 carbon atoms such as polyethylene, polypropylene, ethylene-butene copolymers and the like.

The couplers of the invention can be used in photographic elements and processes like dye-forming couplers have been used in the photographic art.

In the following discussion of suitable materials for use in the emulsions and elements of this invention, reference will be made to *Research Disclosure*, December 1978, Item 17643, published by Industrial Opportunities Ltd., Homewell Havant, Hampshire, P09 1EF, U.K., the disclosures of which are incorporated herein by reference. This publication will be identified hereafter by the term "Research Disclosure".

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents useful in the invention are p-phenylene diamines. Especially preferred are 4-amino-N,N-diethylaniline hydrochloride; 4-amino-3-methyl-N,N-diethylaniline hydrochloride; 4-amino-3-methyl-N-ethyl-N-β-(methanesulfonamido)ethylaniline sulfate hydrate; 4-amino-3-methyl-N-ethyl-N-β-hydroxyethylaniline sulfate; 4-amino-3-β-(methanesulfonamido)-ethyl-N,N-diethylaniline hydrochloride; and 4-amino-N-ethyl-N-(2-methoxyethyl)-m-toluidine di-p-toluenesulfonic acid.

With negative working silver halide, the processing step described above gives a negative image. To obtain a positive (or reversal) image, this step can be preceded by development with a non-chromogenic developing agent to develop exposed silver halide, but not form a dye, and then uniformly fogging the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

Couplers of the invention can be prepared by reactions and methods known in the organic compound synthesis art. A typical synthesis is illustrated by the following example: Synthesis Example A:

The 1-acetyl-6-t-butyl-7-chloro-(3-amino-2,4,6-trimethyl-1-phenyl)-1H-pyrazolo-[3,2-c]-1,2,4-triazole (Compound C) was prepared as described in U.S. Pat. No. 4,777,121. This compound was reacted with ballast acids prepared by known synthetic routes. All compounds prepared provided satisfactory NMR spectra and analytical results. The synthesis of typical examples are as follows:

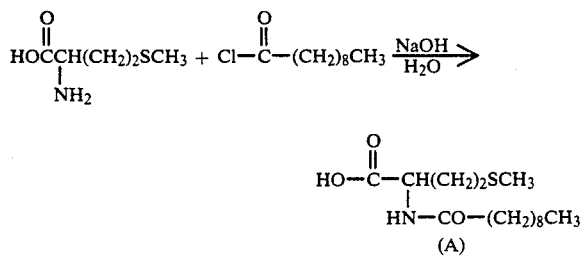

A solution of D,L-methionine (89.6 g, 0.600 mol) and sodium hydroxide (24.0 g, 0.600 mol) in 750 ml water was stirred rapidly in a 2 l flask. The flask was placed in an ice bath and decanoyl chloride (57.2 g, 0.300 mol) was added to the solution all at once. After vigorous stirring for five minutes a solution of 12 g (0.30 mol) NaOH in 150 ml water was added to the emulsion. After two hours the clear solution was acidified to pH 1 with concentrated HCl. The resulting oil was extracted into 2×400 ml ethyl acetate. The ethyl acetate layers were combined and extracted with 200 ml 3N HCl, 100 ml water, and 50 ml of brine. The solution was dried over MgSO₄, filtered, and evaporated to give an oil which began to solidify. The oil was triturated in low boiling ligroin to give, on filtering, 85.2 g of Compound A as a colorless solid, mp 69°-70° C.

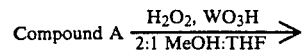

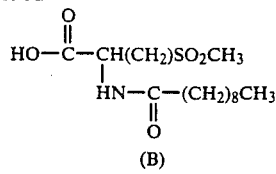

Compound A (50.0 g, 0.165 mol) was dissolved in 250 ml 2:1 methanol:THF (tetrahydrofuran) in a 500 ml flask. A tungstic acid catalyst solution was prepared by adding dropwise enough 50% sodium hydroxide to dissolve a slurry of 1.0 g WO₃.H₂O in 10 ml water. The pH was then lowered to about 5 using a few drops of glacial acetic acid. The resulting translucent solution was added to the stirred reaction solution to give a cloudy mixture. To this was added about one-half of the required amount of 30% hydrogen peroxide (39.3 g, 0.347 mol). An exothermic reaction occurred, and the solution began to boil after about ten minutes. The reaction mixture was cooled briefly to bring the temperature below the boiling point. When the temperature began to diminish, the remaining hydrogen peroxide was added and the flask heated on a hot plate to maintain a temperature of 50°-60° C. The indicated reaction was complete after 1.5 hrs. The reaction mixture was concentrated to give a thick slurry; 300 ml water was added and the solution was filtered and dried to give 53.4 g colorless solid. The product was recrystallized from about 500 ml 5:1 ethyl acetate and ethanol to give 44.4 g (80.3%) Compound B, mp 123°-124° C.

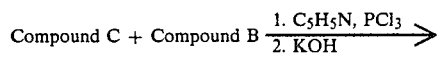

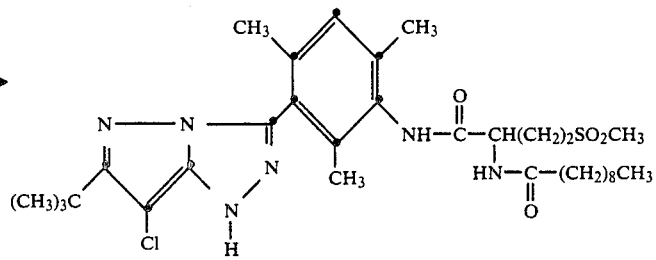

Compound D

Compound C (10.0 g, 26.7 mmol) was dissolved in 50 ml dry pyridine with warming in a 250 ml flask. The solution was stirred under nitrogen in an ice-bath for 15 minutes. A solution of PCl₃ (1.84 g, 13.4 mmol) in 20 ml dry pyridine was added dropwise over 10 minutes to give a light yellow-orange colored solution. The icebath was removed and the solution stirred for one hour. Compound B (8.97 g, 26.8 mmol) was added all at once. The resulting solution was stirred for 15 minutes at room temperature and then placed on a steam bath for 1.5 hrs. The solution was cooled to room temperature and poured into 500 ml water. The product was extracted into 2×250 ml ethyl acetate, the combined ethyl acetate layers was extracted with 2×250 ml 4N HCl, 100 ml water, and 50 ml brine. It was then dried over MgSO₄, filtered, and evaporated to give an oil. The oil was dissolved in 25 ml ethyl acetate and the warm solution saturated with ligroin. After standing overnight, the resulting solid was filtered and washed with 3:1 ligroin:ethyl acetate to give 13.6 g solid, almost pure by TLC (thin layer chromatography) (20% THF in CH₂Cl₂). The solid was chromatographed through 1.4 l silica gel in a 2 l sintered glass funnel eluting with 10% THF in CH$_2$Cl$_2$ to obtain 12.7 g colorless solid, mp 168°–169° C.

The solid (12.0 g, 17.4 mmol) was dissolved in 50 ml 1:1 methanol:THF and treated with a solution of solid KOH (2.52 g, 38.2 mmol) in 15 ml water. After 15 minutes, the solution was acidified with concentrated HCl to pH 1 and the solvents removed under vacuum. The residue was treated with 50 ml water, and the product extracted with 2×200 ml ethyl acetate. The ethyl acetate layers were combined and extracted with 50 ml water and 50 ml brine. The solution was dried over MgSO$_4$, filtered, and evaporated to give glass. Seed crystals were obtained from acetonitrile. The glass was crystallized from 100 ml acetonitrile to give 11.6 g Compound D, mp 138°–139° C. The structure was consistent with analytical data.

Synthesis Example B

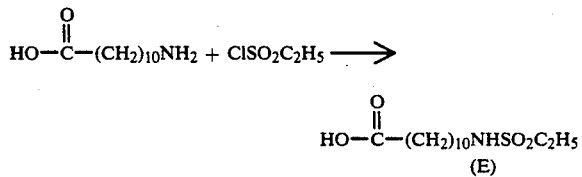

To a 1 l three-necked flask was added 11-aminoundecanoic acid (30.3 g, 0.150 mol), sodium hydroxide (6.0 g, 0.15 mol), and 750 ml water. To the rapidly stirred slurry was added simultaneously over one hour ethanesulfonyl chloride (21.2 g, 0.165 mol) and a solution of sodium hydroxide (6.0 g, 0.15 mol) in 50 ml water. The resulting thick slurry was stirred for an additional hour. The slurry was acidified to pH 1 with concentrated HCl. The product was extracted into 2×250 ml ethyl acetate. The ethyl acetate layers were combined and extracted with 2×100 ml 3N HCl, 100 ml water, and 50 ml brine. The solution was dried over MgSO$_4$, filtered, and evaporated to give a solid. The solid was triturated with 2:1 ligroin:ethyl ether and filtered to obtain 21.0 g Compound E, mp 92°–93° C.

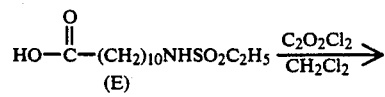

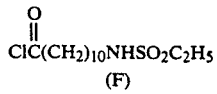

A slurry of Compound E (4.4 g, 15 mmol) in 30 ml methylene chloride was treated with two drops DMF and dropwise with oxalyl chloride (4.1 g, 32 mmol). The slurry was refluxed to give a solution. After the reaction was over the solution was evaporated to give Compound F as an oil which was used immediately.

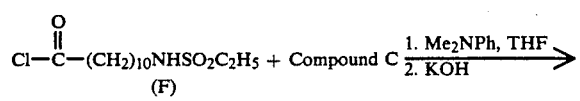

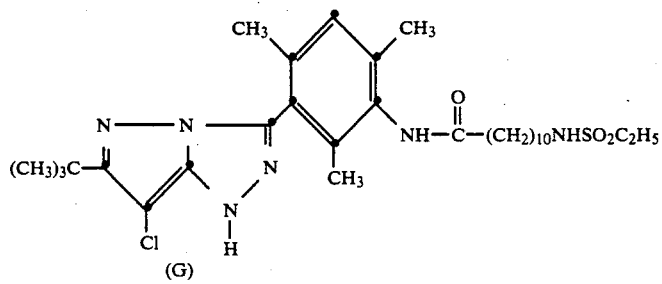

A slurry of Compound C (5.5 g, 14.7 mmol) and dimethylaniline (2.7 g, 22 mmol) in 30 ml dry THF was cooled to 10° C. in an ice bath. The stirred mixture was treated dropwise with Compound F dissolved in 10 ml methylene chloride. After 10 minutes the solution was poured into cold aqueous HCl, and the product extracted into ethyl acetate. The ethyl acetate layer was washed with water and brine. The solution was dried over MgSO$_4$, filtered, and evaporated to give an oil. The oil was chromatographed through silica gel using 5:1 methylene chloride:ethyl acetate to obtain 8.0 g glass which was crystallized from 1:1 heptane:ethyl acetate to give 7.0 g colorless solid. The solid was dissolved in 100 ml 3:1 ethanol:THF and treated with a solution of 1.4 g KOH in 5 ml water. After 15 minutes the solution was poured over cold aqueous HCl, and the product extracted into ethyl acetate. The ethyl acetate was washed with water and brine, dried over MgSO$_4$, and evaporated to give an amorphous solid. The solid was triturated with 4:1 heptane:ethyl ether and filtered to give Compound G. The structure was consistent with NMR and other analytical data.

The following examples further illustrate the invention.

Examples 1–10: Photographic elements were prepared by coating a cellulose acetate-butyrate film support with a photosensitive layer containing a silver bromoiodide emulsion at 0.84 g Ag/sq m, gelatin at 3.77 g/sq m, and one of the couplers designated in Table I dispersed in half its weight of tricresylphospate and coated at 1.62 mmol/sq m. The photosensitive layer was overcoated with a layer containing gelatin at 7.0 g/sq m and bisvinylsulfonylmethyl ether at 1.75 weight percent based on total gelatin. Samples of each element were imagewise exposed through a graduated-density test object and processed at 40° C. employing the processing steps and processing solutions as used in the KODAK E-6 process of Eastman Kodak Company, U.S.A. (KODAK is a trademark of Eastman Kodak Company., U.S.A.) as follows:

| Processing Steps | Time | Temperature |
|---|---|---|
| First development | 3 | 38 |
| Wash | 2 | " |
| Reversal | 2 | " |
| Color development | 6 | " |
| Conditioner | 2 | " |
| Bleach | 6 | " |
| Fixer | 4 | " |
| Final wash | 4 | " |
| Stabilizer | 0.5 | " |

The processing compositions were essentially as described in the British Journal of Photography, 1982 Annual, pages 201–203.

The couplers used in following Table I were as follows:

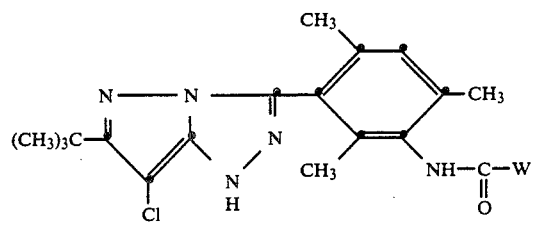

| Example No.: | W: |
|---|---|
| 1 | —CH(CH$_2$)$_2$SO$_2$CH$_3$<br>\|<br>NHCOC$_9$H$_{19}$-n |
| 2 | —CH(CH$_2$)$_2$SO$_2$CH$_3$<br>\|<br>NHCOC$_{11}$H$_{23}$-n |
| 3 | —CH(CH$_2$)$_2$SOCH$_3$<br>\|<br>NHCOC$_{11}$H$_{23}$-n |
| 4 | —CH(CH$_2$)$_2$SO$_2$CH$_3$<br>\|<br>NHCO(CH$_2$)$_8$CH=CH$_2$ |
| 5 | —CH(CH$_2$)$_2$SO$_2$C$_{10}$H$_{21}$-n<br>\|<br>NHCOCF$_3$ |
| 6 | —CH$_2$NHCO(CH$_2$)$_3$SO$_2$C$_{10}$H$_{21}$-n |
| 7 | —(CH$_2$)$_{10}$NHSO$_2$C$_2$H$_5$ |
| 8 | —(CH$_2$)$_{10}$NHPO(OC$_2$H$_5$)$_2$ |
| 9 | —CH(CH$_3$)NHCO$_2$(CH$_2$)$_3$NHSO$_2$C$_8$H$_{17}$-n |
|  | or |
| 10 | —CH(CH$_2$)$_2$SO$_2$CH$_3$<br>\|<br>NH—C—O—C$_{10}$H$_{12}$-n<br>\|\|<br>O |

The formulas of control coupler M-1, comparison couplers M-2 and M-3 were as follows:

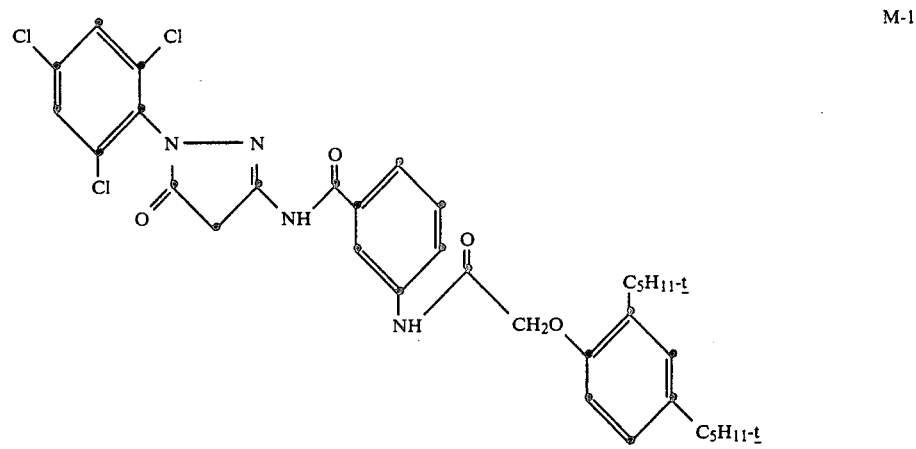

M-1

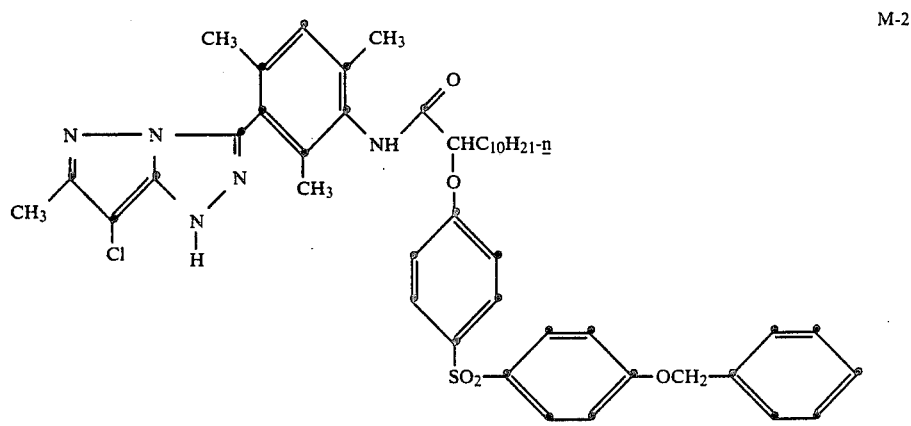

M-2

M-3

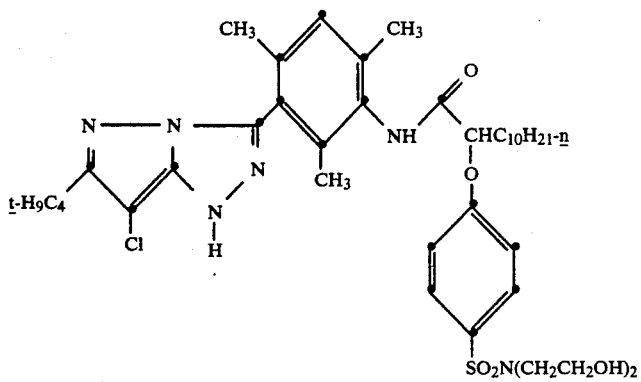

Table I (Coupler Dmax and Gamma Comparisons)

| Example No. Coupler | Dmax | Gamma |
|---|---|---|
| M-1 (control) | 1.28 | 0.63 |
| M-2 (comparison) | 0.96 | 0.43 |
| 1 | 1.61 | 0.70 |
| 4 | 1.88 | 0.77 |
| 5 | 1.53 | 0.60 |
| 6 | 1.46 | 0.50 |
| 9 | 1.03 | 0.40 |
| 10 | 1.24 | 0.50 |
| M-1 (control) | 1.68 | 0.77 |
| M-2 (comparison) | 1.18 | 0.53 |
| 2 | 1.47 | 0.70 |
| M-1 (control) | 1.60 | 0.87 |
| M-2 (comparison) | 1.11 | 0.70 |
| 3 | 2.59 | 1.53 |
| M-1 (control) | 1.48 | 0.83 |
| M-2 (comparison) | 0.58 | 0.23 |
| 7 | 0.53 | 0.17 |
| M-1 (control) | 1.73 | 0.83 |
| M-2 (comparison) | 0.83 | 0.37 |
| 8 | 0.83 | 0.30 |

The general synthesis route for comparison coupler M-2 is described in European Patent Application No. 284,239 and requires more steps than required for synthesis of couplers of the present invention. The ballast group for comparison coupler M-3 also requires more synthesis steps.

The maximum density and gamma of each of the couplers of the invention are as high or higher than those provided by comparison M-2 and M-3.

The invention has been described in detail with particular reference to preferred embodiments thereof, but it will be understood that variations and modifications can be affected within the spirit and scope of the invention.

What is claimed is:

1. A photographic element comprising a support bearing at least one silver halide emulsion layer having associated therewith a pyrazolotriazole dye-forming coupler wherein the coupler contains on a carbon atom in a non-coupling position a ballast group derived from and bonded through a carboxylic acid portion of an unsubstituted or substituted alpha amino acid.

2. A photographic element as in claim 1 wherein the coupler is a 1H-pyrazolo[3,2-c]-1,2,4 triazole coupler.

3. A photographic element as in claim 1 wherein the coupler is represented by the formula:

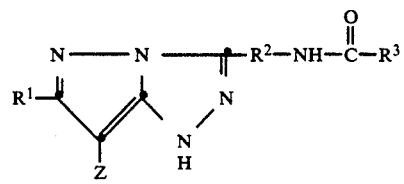

wherein
$R^1$ is an unsubstituted or substituted alkyl group or unsubstituted or substituted aryl group;
$R^2$ is an unsubstituted or substituted phenylene group or alkylidene group;
$R^3$ is a group derived from and bonded through a carboxylic acid portion of an unsubstituted or substituted alpha amino acid; and
Z is hydrogen or a coupling-off group.

4. A photographic element as in claim 1 wherein the coupler is represented by the formula:

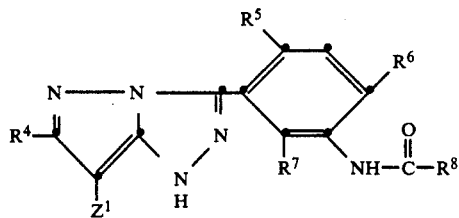

wherein
$R^4$ is a methyl group or t-alkyl group containing 4 to 8 carbon atoms;
$R^5$, $R^6$ and $R^7$ individually are unsubstituted or substituted alkyl containing 1 to 5 carbon atoms or alkoxy containing 1 to 3 carbon atoms;
$Z^1$ is hydrogen or a coupling-off group; and
$R^8$ is a group derived from and bonded through a carboxylic acid portion an unsubstituted or substituted alpha amino acid.

5. A photographic element as in claim 4 whereas $R^8$ is:

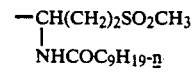

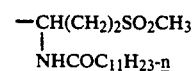

-continued

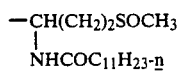

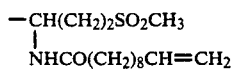

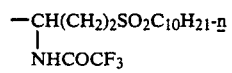

—CH$_2$NHCO(CH$_2$)$_3$SO$_2$C$_{10}$H$_{21}$-n

—CH(CH$_3$)NHCO$_2$(CH$_2$)$_3$NHSO$_2$C$_8$H$_{17}$-n or

-continued

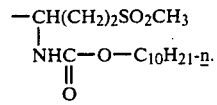

6. A process of developing an image in a photographic element as defined in claim 1 containing an imagewise distribution of developable silver halide grains, said process comprising the step of developing the element with a silver halide color developing agent.

7. A process of developing an image in a photographic element as defined in claim 5 containing an imagewise distribution of developable silver halide grains, said process comprising the step of developing the element with a silver halide color developing agent.

* * * * *